Figure 1:
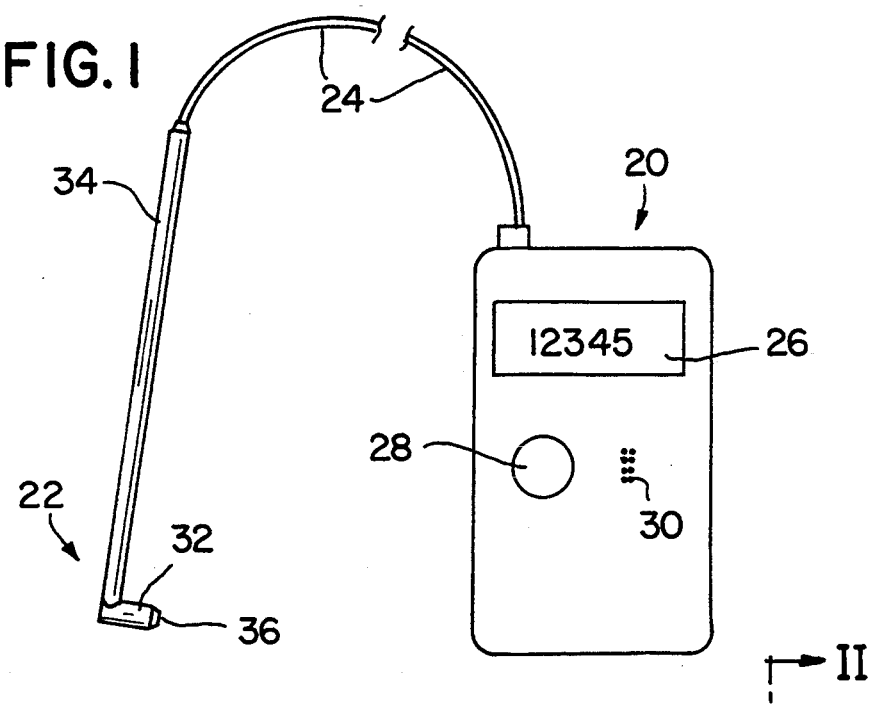

United States Patent [19]
Knapp et al.

[11] Patent Number: 5,427,105
[45] Date of Patent: Jun. 27, 1995

[54] MEASURING PROCEDURE FOR THE THICKNESS OF THE MUCOUS MEMBRANE OF AN ALVEOLAR PROCESS

[75] Inventors: Gerd Knapp, Munich; Benedikt Pollock, Werne; Heiko Bonenkamp, Engelskirchen; Klaus Volkmann, Bergisch-Gladbach, all of Germany

[73] Assignee: Krautkramer GmbH & Co., Germany

[21] Appl. No.: 190,043

[22] PCT Filed: Jul. 22, 1992

[86] PCT No.: PCT/DE92/00593
§ 371 Date: Mar. 31, 1994
§ 102(e) Date: Mar. 31, 1994

[87] PCT Pub. No.: WO93/02623
PCT Pub. Date: Feb. 18, 1993

[30] Foreign Application Priority Data
Aug. 1, 1991 [DE] Germany .................. 41 25 503.8

[51] Int. Cl.⁶ .............................................. A61B 8/00
[52] U.S. Cl. ............................................. 128/660.06
[58] Field of Search ............... 128/660.01, 660.03, 128/660.06, 660.09, 662.03, 662.06, 898

[56] References Cited
U.S. PATENT DOCUMENTS

| | | |
|---|---|---|
| 4,603,702 | 8/1986 | Hwang et al. .......... 128/660.01 |
| 4,674,517 | 6/1987 | Barnes et al. .......... 128/662.03 |
| 4,722,345 | 2/1988 | Ueno et al. ............ 128/660.09 |
| 5,100,318 | 3/1992 | Demyun et al. ........ 128/660.06 |
| 5,161,521 | 11/1992 | Kasahara et al. ....... 128/660.01 |

*Primary Examiner*—George Manuel
*Attorney, Agent, or Firm*—Eckert Seamans Cherin & Mellott

[57] ABSTRACT

The device for measuring the thickness of the mucous membrane in the region of the jawbone ridge consists of an evaluation instrument and a hand probe interconnected by a cable. The hand probe has a probe housing and an ultrasonic oscillator fitted therein on which are arranged a damping member on the back and a lead member on the front, in which the lead member forms a coupling surface for coupling to the mucous membrane and consists of a material with an acoustical impedance corresponding to 0.3 to 3 times the value and preferably 0.5 to 2.4 times the value of the acoustical impedance of water. A control electronic system and an evaluation electronic system, an electric power supply and a display unit are fitted in the evaluation instrument.

5 Claims, 1 Drawing Sheet

MEASURING PROCEDURE FOR THE THICKNESS OF THE MUCOUS MEMBRANE OF AN ALVEOLAR PROCESS

The invention relates to a measuring procedure for the thickness of the mucous membrane of an alveolar process. Dentists require a measurement of the thickness of the mucous membrane in order, before implantation of screw cores, e.g. titanium screw cores, in an alveolar process, to be able to determine the actual thickness of the alveolar process in order for certainty to exist that enough bone material is present for a durable implant. According to the state of the art, the thickness of the mucous membrane is determined with a penetrating body (needle); for this purpose the mucous membrane is pierced and one determines what path the needle covers until it encounters the alveolar process. This procedure is not only painful but also entails the risk of an infection.

From EP-A 0 353 209 a device is known for the inspection of teeth by ultrasound with which the teeth to be tested are scanned by an array of ultrasonic oscillators. Between the array and the gum a front-running body is arranged which may consist essentially of water or the like.

U.S. Pat. No. 4,603,702 shows a circuit which can be used for measuring how long a patient is exposed to ultrasound. The circuit can distinguish whether an ultrasonic oscillator is coupled to a patient or to air. The sound exposure time is measured as long as the ultrasonic oscillator is coupled to the patient.

The invention has the objective of devising a measuring procedure which can be operated without damaging the mucous membrane.

The procedure according to the invention operates with ultrasound according to the pulse-echo procedure, also called the pulse-reflection method. For ultrasonic measuring procedures in general, reference is made to the German book: J. Krautkrämer and H. Krautkrämer, "Material testing with ultrasound", 4th ed., Springer Verlag. The ultrasonic oscillator arranged in the probe housing of the measuring device periodically emits ultrasonic pulses which pass through the probe tip and enter the mucous membrane from its coupling surface. The pulses are reflected at the transition (interface) between mucous membrane and alveolar process surface. The thickness of the mucous membrane is determined from the travel time of the sound by using the known velocity of sound (about 1500 m/s).

A qualitatively good coupling of the coupling surface with the mucous membrane is achieved according to the invention by manufacturing the probe tip from a material which has acoustic impedance similar to that of the mucous membrane. This is a tissue and therefore, in ultrasound, has essentially the same properties as water. If the probe tip is in good contact with the mucous membrane, no or only a small jump (sound hardness jump) on the coupling surface/mucous membrane surface interface occurs in the acoustic impedance with the result that practically no sound is reflected there. The criterion of low or absent sound reflection at the transition between coupling surface and mucous membrane is utilized in order to distinguish between good and poor couplings. A measurement is performed only if the coupling is good, therefore if the echo from the coupling surface/mucous membrane surface interface is below a threshold value.

In order to make certain that the echo from the coupling surface is normally present, this echo is registered during the calibration phase in which the coupling surface is free and in contact only with air. It must display only a certain amplitude. In this case not only one echo, i.e., preferably the first echo of the coupling surface is registered during the calibration phase and evaluated, but also a subsequent, preferably the second, echo from the coupling surface is also evaluated. During the calibration phase the coupling surface should be totally free; it may not be covered with water droplets or dirt but rather exposed exclusively to air. However, if it is coated or covered in any way, then this is manifested in the fact that the ratio from two consecutive echoes is changed. The ratio of two echoes is therefore, according to the invention, used to ascertain that the coupling surface is actually free during the calibration phase.

In a modification, at the same time the amplitude of the echo of the coupling surface is utilized in order to control the emission energy. The electrical energy periodically transmitted to the ultrasonic oscillator is dimensioned such that the echo from the coupling surface displays a certain amplitude. This control or modulation of the emission energy also has the advantage that the control switch for the emission energy does not compensate for the lack of acoustic reflection on the coupling surface by increasing the emission energy. A real measurement takes place only when consecutive echoes from the coupling surface during the calibration phase do not deviate from one another so much that a (second) threshold value is not reached. However, if the threshold is not reached, an error signal is emitted and the actual measurement is blocked.

It has been found to be advantageous if the evaluation electronic system of the evaluator emits acoustic signals for a poor coupling and for a successfully performed measurement. In practical use of the measuring instrument the operator must focus his concentration on finding and touching the correct places on the mucous membrane. When so doing he cannot also observe the evaluator. To this extent an acoustic report is advantageous. In the same manner it is advantageous if the evaluator after receipt of a successful measurement indicates the registered thickness of the mucous membrane by an acoustic signal until a new measurement is begun or the measurement is completely stopped. In this way, the operator, generally a dentist, can concentrate totally on using the probe.

On the whole, the measuring device according to the invention is constructed and designed in such a way that the ultrasonic measuring procedure requires no particular attention, rather the device is self-controlled to the extent that if the coupling is adequate and if a reasonable echo from the surface of the alveolar process is present, a measurement is performed, but if the coupling and/or echo from the alveolar process are unsatisfactory, no measurement is performed, so that no incorrect measurement can be obtained.

The material for the probe tip should have acoustic impedance (sound hardness) lying in the proximity of the value of the acoustic impedance of water. In this way the distinct difference between a coupling to a mucous membrane and a measurement against air is made possible according to the invention. The material for the probe tip can be selected as follows: with a totally clean front surface (no water drops or dirt particles on it) the height of the first echo (or another echo) from the coupling surface of the probe tip is measured against air. Then, while holding all other parameters constant, the probe tip with its front surface is totally immersed in water. The level of the echo emitted should then be smaller than 20%, preferably smaller than 5%, of the value measured against air. The material is selected according to these criteria.

The material for the probe tip should also have an acoustic velocity that is as low as possible, therefore as close as possible to the velocity of sound in water. In this way the probe tip can be made short.

Preferably, in order to perform a valid measurement at least one coupling must exist for the duration of three measurement cycles. If the coupling can exist only for a shorter time, an error is indicated. Preferably the instrument reports on several individual measured values and sends the average value to the indicator.

It has been found to be very advantageous to start and run the calibration phase automatically; it is triggered by the electronic control system. The calibration phase in each case takes place when the device is newly switched on or when the plug connection of the cable between the hand-held probe and the evaluator is made with the evaluator switched on.

Figure 2:
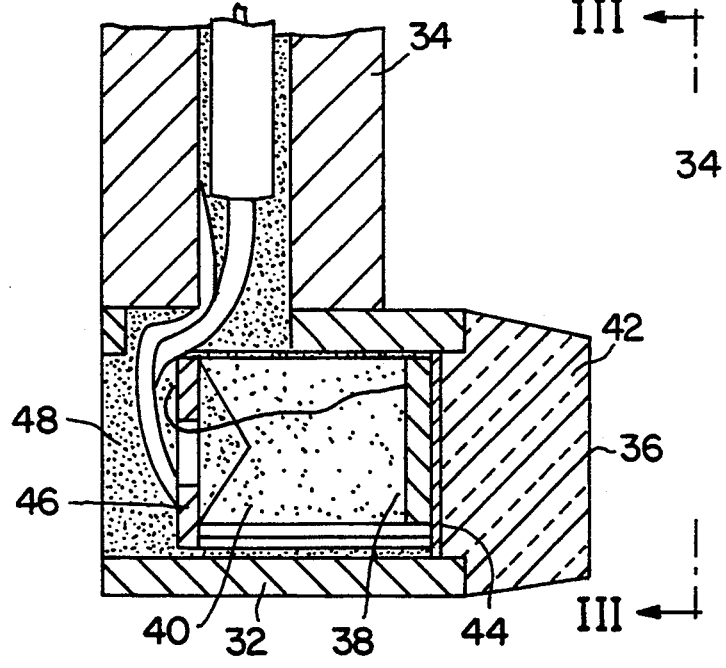
Figure 3:
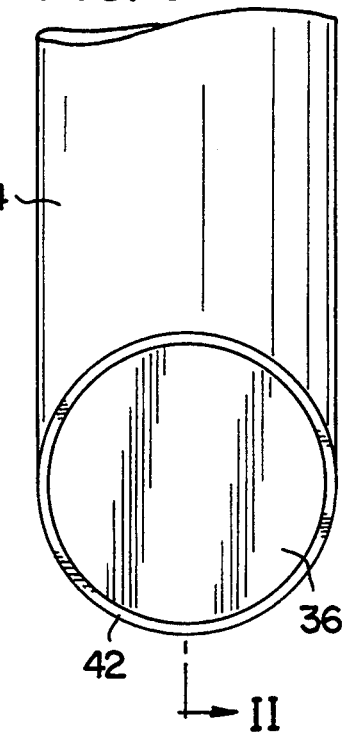

An advantageous example of the measurement device according to the invention which also serves to illustrate the measuring procedure of the invention and is not to be considered limiting, is described in detail in the following with reference to the drawing, where:

FIG. 1 shows a top view of the entire instrument,
FIG. 2 is a section along line II—II in FIG. 3, and
FIG. 3 is a view along III—III in FIG. 2.

As FIG. 1 shows, the complete measuring instrument consists of a convenient evaluating device 20 which is about the size of the hand, and a probe 22, both of which are detachably connected to one another by a cable 24. In the evaluator 20 an indicator 26 is installed with an LCD (liquid crystal display) as well an on-off switch 28 and (concealed under openings) a signal emitter 30. Furthermore, a control-evaluation electronic system and a voltage source is installed in the housing of the evaluator 20.

The hand-held probe 22 consists of a first housing part 32 forming the bottom end and a second housing part 34. The first housing part is described in detail in the following; it is visible especially in FIGS. 2 and 3. The two housing parts are made from a polysulfone pipe, white, with 6 mm outer diameter. The second housing part 34 has a length of about 150 mm; the first housing part 32 is about 10 mm long. As FIG. 1 shows the two housing parts 32 and 34 form an L-shaped arrangement. The end face of the free end of the first housing part 32 is the coupling surface 36 which will be discussed below. The two housing parts 32, 34 are connected to one another in such a way that no gap exists between them; the interior space of the two housing parts 32, 34 is filled with a suitable filling mass, e.g., silicone.

In the first housing part 32 an ultrasonic oscillator 38 (piezo-vibrator) is arranged at right angles to the pipe axis of the first housing part 32; it has a diameter of about 3.3 mm and is designed for 5 MHz. To the rear a muffler 40 is connected to it; it has a conical taper to prevent reflections from its surface. On the other sound-emitting surface of the ultrasonic oscillator 38 probe tip 42 is arranged. It is made from polymethylpentene. This material has an acoustic impedance which lies close to the acoustic impedance of water. It is also well suited for medical applications. As FIG. 2 shows, the probe tip 42 has essentially the shape of a truncated cone, but on the whole, a diameter, even in the region of its coupling surface 36, greater than the diameter of the ultrasonic oscillator 38. The coupling surface 36 is flat. Between the probe tip 42 and the ultrasonic oscillator 38 is another adaptation layer 44. It is metallic and serves simultaneously for contacting, as FIG. 2 shows. The back side of the ultrasonic oscillator 38 is metal-plated. It is contacted via a junction line. The junction lines are guided to a soldered support point 46 located on the back side of the muffler 40. From there the junction line runs in the form of a coaxial lead wire. The region behind the soldered support point 46 where the junction lines are located is filled with a filling mass 48 in such a way that an essentially flat closure is achieved. The second housing part 34 holds the junction lines and also serves as a handle for the hand-held probe.

The transmitter of the measuring instrument consists of a spike pulser with a switching transistor; in this case the transmitting voltage is generated by inductance which is in resonance with a charging condenser. In a first cycle the inductance is applied for an adjustable time via switching elements to a voltage of 5 volts. In a second cycle, the inductance is wired parallel to the charging condenser. After a quarter period of this oscillation cycle when the energy from the coil has passed to the condenser, the condenser is discharged via a damping resistor and the ultrasonic oscillator 38. In this the ultrasound emission pulse is generated. The emission energy is approximately proportional to the energy stored in the coil, the latter in turn is determined by the time for which the voltage of 5 volts is applied. This time is governed in steps of 250 ns.

The receiver consists of two series-connected amplifiers with a total of 30 dB amplification. The outputs of the two amplifiers are each connected with comparators. The first amplifier detects the echoes of the coupling surface 36; the second amplifier detects the echoes from the surface of the alveolar process.

In the electronic evaluation system two time gates (shutters) are provided, i.e., one shutter for the first echo of the coupling surface 36 and a shutter for the following echo. The first shutter opening is between 2.5 and 4.0 $\mu$s and the second opening is between 4.0 and 7.0 $\mu$s behind the emission pulse during the calibration phase. If no echo signal above a measurement threshold is present, a first error signal is emitted. If only one of the two echo signals is not above the threshold, a second error signal is emitted. In both cases a measurement process is not permitted.

During the calibration phase the emission amplitude is successively reduced in such a way that the amplitude of the first echo just reaches the measurement threshold. This value is stored for the following procedures. Therefore the sensitivity is calibrated.

With this emission amplitude subsequently the lag time of the probe, therefore especially of the probe tip 42, is measured and stored.

During the actual measurement in the system cycle of 128 ms periodically emission pulses are generated with the calibrated value. The openings during the measurement for the coupling surface echo are set at a time between the measured pre-running time and the measured pre-running time plus 0.5 $\mu$s and for the second opening echo to the measured pre-running time plus 0.5 $\mu$s and the measured pre-running time plus 10.75 $\mu$s. In addition a time gate is also provided for the measurement into which the echoes from the bone surface must enter; it is designed in such a way that mucous membrane thicknesses between e.g., 0.5 and 0 mm can be registered, but the measurement range can also be expanded or reduced to other ranges.

The measured value evaluation range, therefore the range in which the echo from the alveolar process must fall, is preferably provided with a measurement threshold which is designed such that noise signals cannot lead to a measurement.

In one version, not shown, the second housing part 34 is flexibly adjustable, e.g., designed as a gooseneck. Therefore it can be shaped by hand but retains the set bend during practical use.

We claim:

1. A method for measuring a mucous membrane of an alveolar process, the mucous membrane having an acoustic impedance, the method comprising the steps of:
    selecting a probe tip which:
        is made of material having an acoustic impedance that matches as close as possible the acoustic impedance of the mucous membrane, and,
        forms a coupling-surface;
    emitting acoustic pulses from an ultrasonic oscillator, which operates in accordance with the pulse-echo process, through the probe tip;
    calibrating, which comprises the steps of:
        exposing the coupling-surface to air,
        monitoring echoes of the acoustic pulses from the coupling-surface,
        evaluating in amplitude one echo and a subsequent echo,
        emitting an error signal if a ratio of the amplitudes between said one echo and said subsequent echo drops below a pre-determined threshold value, and,
        if no error signal, then, registering the amplitude of one of said one echo and said subsequent echo,
    measuring, which comprises the steps of:
        coupling the coupling-surface of the probe tip with the mucous membrane,
        monitoring echoes of the acoustic pulses from coupling-surface,
        evaluating in amplitude the echoes of the acoustic pulses from the coupling-surface, and,
        if on condition that the amplitudes of the echoes of the acoustic pulses from the coupling-surface evaluated during measuring are clearly smaller than the amplitude registered during calibrating, then, permitting whenever said condition is satisfied a given signal with the evaluated amplitudes encoded thereon to pass to an evaluator that determines a thickness of the mucous membrane from the signal.

2. The method of claim 1, further comprising the step of:
    dimensioning electrical energy that is periodically transmitted to the ultrasonic oscillator such that echoes from the coupling-surface have a certain amplitude.

3. The method of claim 1, further comprising the steps of:
    one of enabling and disabling an emitter of an acoustic signal; and,
    if, during coupling, the amplitudes of the echoes of the acoustic pulses from the coupling-surface evaluated during measuring satisfy said condition, then the other of enabling and disabling the emitter of the acoustic signal.

4. The method of claim 1, further comprising the step of:
    emitting an error indication if the step of coupling has a duration that is shorter than a predetermined time.

5. The method of claim 1, further comprising the step of:
    starting the step of calibrating at the exclusion of the step of measuring, and stepping through the steps of calibrating, on each occurrence of one of:
        a plug connection being formed between a hand-held probe and an evaluator while the evaluator is supplied with power, and,
        the evaluator being newly supplied with power while the plug connection is formed with the hand-held probe.

* * * * *